(12) United States Patent
Iwamoto et al.

(10) Patent No.: US 10,676,447 B2
(45) Date of Patent: Jun. 9, 2020

(54) BENZOTRIAZOLE DERIVATIVE COMPOUND AND THE USE THEREOF

(71) Applicant: SHIPRO KASEI KAISHA, LTD., Sakai, Fukui (JP)

(72) Inventors: Takuya Iwamoto, Sakai (JP); Toshiyuki Uesaka, Sakai (JP)

(73) Assignee: SHIPRO KASEI KAISHA, LTD., Sakai (JP)

( * ) Notice: Subject to any disclaimer, the term of this patent is extended or adjusted under 35 U.S.C. 154(b) by 0 days.

(21) Appl. No.: 16/499,786

(22) PCT Filed: Mar. 16, 2018

(86) PCT No.: PCT/JP2018/010571
§ 371 (c)(1),
(2) Date: Sep. 30, 2019

(87) PCT Pub. No.: WO2018/180632
PCT Pub. Date: Oct. 4, 2018

(65) Prior Publication Data
US 2020/0031782 A1 Jan. 30, 2020

(30) Foreign Application Priority Data
Mar. 29, 2017 (JP) ................. 2017-066478

(51) Int. Cl.
*C07D 249/20* (2006.01)
*C08K 5/3475* (2006.01)

(52) U.S. Cl.
CPC .......... *C07D 249/20* (2013.01); *C08K 5/3475* (2013.01)

(58) Field of Classification Search
CPC .................................................. C07D 249/20
See application file for complete search history.

(56) References Cited

U.S. PATENT DOCUMENTS

| 3,738,837 A | 6/1973 | Kuwabara et al. |
| 2010/0103352 A1 | 4/2010 | Suzuki et al. |

FOREIGN PATENT DOCUMENTS

| JP | H07-118378 A | 5/1995 |
| JP | 2005-290240 A | 10/2005 |
| JP | 2011-190293 A | 9/2011 |
| JP | 2012-041333 A | 3/2012 |
| JP | 2014-144932 A | 8/2014 |
| WO | WO 2008/126700 A1 | 10/2008 |

OTHER PUBLICATIONS

International Search Report for PCT/JP2018/010571 (PCT/ISA/210) dated May 29, 2018, with English translation.
Written Opinion of the International Searching Authority for PCT/JP2018/010571 (PCT/ISA/237) dated May 29, 2018.

*Primary Examiner* — Joseph R Kosack

(74) *Attorney, Agent, or Firm* — Birch, Stewart, Kolasch & Birch, LLP (57) ABSTRACT

The present invention provides a benzotriazole derivative compound represented by a general formula,

[Chemical 1]

General formula (1)

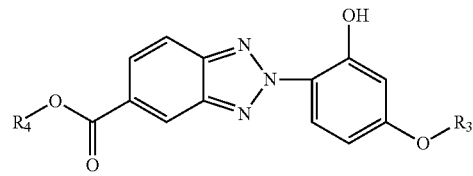

(wherein R3 represents an alkyl group, and R4 represents an acryloyloxyalkyl group or a methacryloyloxyalkyl group), as a novel compound capable of being suitably used as a highly light-resistant ultraviolet absorber or resin composition that exhibits an ultraviolet-blocking function over a prolonged period of time and that strongly absorbs wavelengths in the ultraviolet light range of 400 nm or less while ensuring little coloration.

3 Claims, 6 Drawing Sheets

BENZOTRIAZOLE DERIVATIVE COMPOUND AND THE USE THEREOF

TECHNICAL FIELD

The present invention relates to a new benzotriazole derivative compound and the use thereof. In more detail, the present invention relates to an ultraviolet light absorber or a resin compound ensuring little coloration, while exhibiting a maximum absorption wavelength in a vicinity of 360 nm and strongly absorbing ultraviolet light range of 400 nm or less.

BACKGROUND ART

It is well known that organic materials such as a resin and the like degrade by a function of ultraviolet light of solar light. In the resin, coloration or decrease in strength occurs by the ultraviolet light, and in a variety of functional organic materials, decomposition is caused by the ultraviolet light and their functions degrade.

In order to prevent the degradation of these organic materials caused by the ultraviolet light, an ultraviolet light absorber is generally used. For example, in a display device, it is generally practiced to add the ultraviolet light absorber to optical films such as polarizer protective films and the like thereby preventing the coloration of these optical films. Also, in order to prevent the degradation of a near-infrared light absorber included in anti-reflection films caused by the ultraviolet light, the ultraviolet light absorber is added to the anti-reflection films. Further, a variety of organic materials such as fluorescent elements, phosphorescent elements, and the like are used in a luminous element of organic EL displays. That is to say, in order to prevent the degradation of the organic materials caused by the ultraviolet light, the ultraviolet absorber is added to a surface film of the display.

In human bodies, it is well known that skins and eyeballs get tanned by the ultraviolet light, causing various maladies. The bad effect to the eyeballs caused by the ultraviolet light includes, for example, a possible development of a cornea inflammation when the eyes are exposed to solar light in such an outdoor place where there are lots of ultraviolet light. As for the bad effect to lens, a cataract might be developed by the accumulated ultraviolet light.

In order to prevent various diseases related to eyeballs caused by the ultraviolet light, it is generally practiced to add the ultraviolet absorber to glass lens or contact lens, thereby preventing the ultraviolet light from reaching the eyes.

In each of the above mentioned uses, it is required to fully block the ultraviolet light. In other words, it is required to fully block the solar light of 400 nm or less. It is known that conventionally used ultraviolet light absorbers have weakness in that they do not fully absorb a long wavelength range of 350 to 400 nm, in particular, 380 to 400 nm, and therefore, many ultraviolet light absorbers have been proposed that could efficiently absorb the ultraviolet light in these long wavelength ranges. For example, as described in patent documents 1 to 3, benzooxadinone derivatives, triazine derivatives, benzotriazole derivatives, and the like, have been proposed in each of the above mentioned uses. However, benzooxadinone derivatives described in patent document 1 have generally low light resistance, and therefore, it is anticipated that the ultraviolet light absorbing property degrades with a long team use. In addition, triazine derivatives and benzotriazole derivatives described in patent documents 2 and 3 have low long wavelength range absorption property, and therefore, the ultraviolet absorbing function is not sufficient.

Patent documents 4 to 5 describe that, by modifying benzotriazole with sesamol, the light of the long wavelength range can be efficiently absorbed. However, it is difficult to apply it for each of the above mentioned uses, since the absorption of visible light range of 400 to 420 nm is strong, and therefore, the optical film or glass lens turns yellow when the above mentioned compound is added to them.

PRIOR ART DOCUMENTS

Patent Documents

Patent document 1: Official Gazette, Patent Publication No 2004-10875
Patent document 2: Official Gazette, Patent Publication No 2010-168462
Patent Document 3: Official Gazette, Patent Publication No 2004-325511
Patent Document 4: Official Gazette, Patent Publication No 2012-41333
Patent Document 5: Official Gazette, Patent Publication No 2012-25680

SUMMARY OF THE INVENTION

Problem to be Solved by the Invention

In view of the above situations, the object of the present invention is to provide a new compound ensuring little coloration, while exhibiting strongly absorbing ultraviolet light range of 400 nm or less. Further, the object of the present invention is to provide a new compound that can preferably be used as an ultraviolet absorber and a resin compound that have a high light resistance exhibiting an ultraviolet blocking function in a long term.

Means to Solve the Problem

As a result of intensive studies to solve the above mentioned problem, the inventors of the present invention have found that benzotriazole derivative compound as represented by the following general formula (1) plays an important role to solve the problem above.

[Chemical 1]

General formula (1)

[in the general formula (1), $R_3$ represents an alkyl group whose carbon number is 1 to 8, $R_4$ represents an acryloyl oxyalkyl group whose alkyl carbon number is 1 to 2 or an methacryloyl oxyalkyl group whose alkyl carbon number is 1 to 2.]

Effect of the Invention

Benzotriazole derivative compound represented by general formula (1) of the present invention is useful as an ultraviolet absorber that can solve the problem in the prior art, since it shows a maximum absorbing wavelength in the vicinity of 360 nm, causes little coloration while strongly absorbing the ultraviolet light, and has a high light-resistance that shows the ultraviolet light blocking function in a long term.

BEST EMBODIMENT FOR CARRYING OUT THE INVENTION

Hereinafter, the detailed explanations are given for the present invention. In the present invention, as an ultraviolet light absorber and as a resin compound, benzotriazole derivative compound represented by general formula (1) is used. Hereinafter, the explanations are given for the compound represented by general formula (1).

[Chemical 1]

General formula (1)

In benzotriazole derivative compound represented by general formula (1), $R_3$ represents an alkyl group whose carbon number is 1 to 8, $R_4$ represents an acryloyl oxyalkyl group whose alkyl carbon number is 1 to 2 or an methacryloyl oxyalkyl group whose alkyl carbon number is 1 to 2.]

As an example of the general formula (1) of benzotriazole derivative compound of the present invention, the following can be exemplified. 2-acryloyl oxyethyl 2-(2-hydroxy-4-methoxyphenyl)-2H-benzotriazole-5-carbocylate, 2-methacryloyl oxyethyl 2-(2-hydroxy-4-methoxyphenyl)-2H-benzotriazole-5-carbocylate, 2-methacryloyl oxyethyl 2-(2-hydroxy-4-octyloxyphenyl)-2H-benzotriazole-5-carbocylate.

Although a method of synthesizing general formula (1) of the benzotriazole derivative compound of the present invention is not specifically limited and a publicly known reaction principle can be used, it is in particular preferable to take a step of reacting 4-carboxy-2-nitro benzene diazonium salt with 1,3-dimethoxy benzene represented by formula (2) below.

[Chemical 2]

General formula (2)

In the following (chemical 3 to chemical 11), an example of a reaction path is shown by which general formula (1) of the benzotriazole derivative compound of the present invention is obtained. In the following, X represents a halogen atom. By going through the reaction process in particular of (Chemical 4), general formula (1) of benzotriazole derivative compound of the present invention can be obtained with high yield.

[Chemical 3]

[Chemical 4]

[Chemical 5]

-continued

[Chemical 6]

[Chemical 7]

[Chemical 8]

[Chemical 9]

-continued

[Chemical 10]

[Chemical 11]

In the benzotriazole derivative compound of the present invention, homopolymerization or copolymerization is available. Although other polymerizable monomers that can be copolymerizable are not limited, acrylic ester such as methyl acrylate, ethyl acrylate, propyl acrylate, butyl acrylate, hexyl acrylate, and octyl acrylate, and methacrylate ester such as methyl methacrylate, ethyl methacrylate, propyl methacrylate, butyl methacrylate, hexyl methacrylate, and octyl methacrylate can be exemplified.

Although the benzotriazole derivative compound of the present invention is not specifically limited, α olefin polymer or ethylene-vinyl acetate copolymer such as polyethylene, polypropylene, polybutene, polypentene, poly-3-methyl butylene, and polymethyl pentene, polyolefin such as ethylene-propylene copolymer, polyvinyl chloride, polyvinyl bromide, polyvinyl fluoride, chlorinated polyethylene, chlorinated polypropylene, brominated polyethylene, chlorinated rubber, vinyl chloride-vinyl acetate copolymer, vinyl chloride-ethylene copolymer, vinyl chloride-propylene copolymer, vinyl chloride-styrene copolymer, vinyl chloride-isobutylene copolymer, vinyl chloride-vinylidene copolymer, vinyl chloride-styrene-maleic anhydride ternary copolymer, vinyl chloride-styrene-acrylonitrile ternary copolymer, vinyl chloride-butadiene copolymer, vinyl chloride-isobutylene copolymer, vinyl chloride-chlorinated propylene copolymer, vinyl chloride-vinylidene chloride-vinyl acetate ternary copolymer, vinyl chloride-acrylic ester copolymer, vinyl chloride-maleic ester copolymer, vinyl chloride-methacrylate ester copolymer, vinyl chloride-acrylonitrile copolymer, halogen containing synthetic resin such as internal plasticity polyvinyl chloride, petroleum resin, coumarone resin, polystyrene, copolymer of styrene and other monomer (such as maleic anhydride, butadiene, acrylonitrile), styrene resin such as acrylonitrile-butadiene-styrene resin, acrylic ester-butadiene-styrene resin, and methacrylic ester-butadiene-styrene resin, polyvinyl acetate, polyvinyl alcohol, polyvinyl formal, polyvinyl butyral, acrylic resin, methacrylic resin, polyacrylonitrile, polyphenylene oxide, polycarbonate, denaturalized polyphenylene oxide, polyacetal, phenolic resin, urea resin, melamine resin, epoxy resin, silicone resin, polyethylene terephthalate, reinforced polyethylene terephthalate, polybutyrene terephthalate, polysulfone resin, polyether sulfone, polyphenylene sulfide, polyether ketone, polyether imide, polyixy benzoile, polyimide, polymareimide, polyamide imide, alkyd resin, amino resin, vinyl resin, er soluble resin, powder paint resin, polyamide resin, polyurethane resin, polythiourethane resin, unsaturated polyester resin can be exemplified.

In adding the benzotriazole derivative compound of the present invention to a resin, as an ultraviolet light absorber, only the benzotriazole derivative compound of the present invention can be used or it can be used in combinations with other ultraviolet light absorbers. Regarding ultraviolet light absorbers other than the benzotriazole derivative compound of the present invention, they are not specifically limited and they can be used as far as they can be obtained in general markets and as far as they can absorb the ultraviolet region. For example, benzotriazole derivatives, benzophenone derivatives, salicylate derivatives, cyanoacrylate derivatives, triazine derivatives and the like are used. The ultraviolet light absorber can be used alone or two or more of them can be mixed together, as appropriate.

The benzotriazole derivative compound of the present invention can be used by 0.01 to 10 wt % with respect to the resin, and preferably by 0.1 to 1 wt % with respect to the resin.

EXAMPLES

Hereinafter, a method of synthesizing the benzotriazole derivative compound experimented in the present invention, and properties of the compound are shown. However, the present invention is not limited to these embodiments.

Example 1

Intermediate; synthesis of 5-carboxy-2-(2,4-dimethoxyphenyl)-2H-benzotriazole

[Chemical 12]

To a four-neck flask of 2000 ml, a balled condenser, a thermometer, and a mixing device were attached, in which 875 ml of water, 56.5 g (0.533 mol) of sodium carbonate, 178.8 g (0.982 mol) of 4-amino-3-nitro benzoic acid were put and dissolved, to which 197.1 g (1.028 mol) of an aqueous solution of 36% sodium nitrite were added. To a four-neck flask of 3000 ml, a balled condenser, a thermometer, and a mixing device were attached, in which 875 ml of water and 372.0 g (2.370 mol) of 62.5% sulfuric acid were mixed and cooled to 3 to 7° C., onto which the mentioned solution was dripped, followed by mixing it at the same temperature for 1 hour to obtain an aqueous solution of diazonium salt. To a four-neck flask of 5000 ml, a balled condenser, a thermometer, and a mixing device were attached, in which 139.4 g (1,009 mol) of 1,3-dimethoxybenzene, 900 ml of isopropyl alcohol, and 390 g of water were put and mixed, onto which an aqueous solution of diazonium salt was dripped at 5 to 10° C. for 2 hours, further followed by mixing for 15 hours at 10 to 15° C. 280 ml of an aqueous solution of 32% sodium hydroxide was added thereto, followed by removing a water layer in a bottom layer at 70° C., further followed by obtaining a sediment generated by adding 75 ml of isopropyl alcohol and 875 ml of water, further followed by filtering, rinsing and drying to obtain 218.3 g of 6-(4-carboxy-2-nitrophenylazo)-1,3-dimethoxybenzene.

To a four-neck flask of 3000 ml, a balled condenser, a thermometer, and a mixing device were attached, in which 217.8 g (0.657 mol) of 6-(4-carboxy-2-nitrophenyl azo)-1, 3-dimethoxybenzene, 147.6 g (1.181 mol) of an aqueous solution of 32% sodium hydroxide, 370 ml of water, 1100 ml of isopropyl alcohol, and 1.1 g of hydroquinone were put, followed by dripping 52.6 g (0.630 mol) of 60% hydrazine monohydrate at 70° C. for 1 hour, followed by mixing at the same temperature for 3 hours. Then the pH value was adjusted to 3 by 62.5% sulfuric acid, followed by removing a water layer in a bottom layer at 70° C., further followed by cooling the obtained organic layer to 25° C. to which 820 ml of water was added, followed by mixing for 1 hour, further followed by filtering, rinsing, and drying the generated sediment, thereby obtaining 158.9 g of 5-carboxy-2-(2,4-dimethoxyphenyl)-2H-benzotriazole N-oxide.

To a four-neck flask of 3000 ml, a balled condenser, a thermometer, and a mixing device were attached, in which 156.8 g (0.497 mol) of 5-carboxy-2-(2,4-dimethoxyphenyl)-2H-benzotriazole N oxide, 780 ml of isopropyl alcohol, 780 ml of water, and 295.8 g (2.366 mol) of an aqueous solution of 32% sodium hydroxide were put, to which 255.9 g (2.367 mol) of a thiourea dioxide was added at 70 to 80° C. taking for 30 minutes. It was mixed at the same temperature for 2 hours, and the pH value was adjusted to 4 with 62.5% sulfuric acid, followed by removing the water layer in the bottom layer by separating it, further followed by adding 480 ml of isopropyl alcohol and 480 ml of water, further followed by cooling the obtained organic layer to 25° C., further followed by filtering, rinsing, and drying the generated sediment, thereby obtaining 107.4 g of 5-carboxy-2-(2, 4-dimethoxyphenyl)-2H-benzotriazole. The yield was 37% (from 4-amino-3-nitro benzoic acid).

Example 2

Intermediate; synthesis of 5-carboxy-2-(2-hydroxy-4-methoxyphenyl)-2H-benzotriazole

[Chemical 13]

To a four-neck flask of 2000 ml, a balled condenser, a thermometer, and a mixing device were attached, in which 107.1 g (0.358 mol) of 5-carboxy-2-(2,4-dimethoxyphenyl)-2H-benzotriazole, 540 ml of acetic acid, 365.2 g (2.327 mol) of 62.5% sulfuric acid, 221.8 g (2.148 mol) of 95% sulfuric acid were put and dissolved, to which 480 ml of water was added, followed by mixing at 130 to 140° C. for 20 hours, further followed by adding 480 ml of water to filter and rinse the sediments, thereby obtaining a coarse crystal. The obtained coarse crystal was repulp-washed with 130 ml of isopropyl alcohol and 300 ml of 4-methyl-2-pentanon to obtain 59.5 g of 5-carboxy-2-(2-hydroxy-4-methoxyphenyl)-2H-benzotriazole. The yield was 58% (from 5-carboxy-2-(2,4-dimethoxyphenyl)-2H-benzotriazole).

Example 3

Synthesis of compound [a]; 2-methacryloyloxyethyl 2-(2-hydroxy-4-methoxyphenyl)-2H-benzotriazole-5-carboxylate

[Chemical 14]

Compound (a)

To a four-neck flask of 2000 ml, a balled condenser, a balled condenser, a thermometer, and a mixing device were attached, to which 59.5 g (0.209 mol) of 5-carboxy-2-(2-hydrocy-4-methoxyphenyl)-2H-benzotriazole, 900 ml of toluene, 3.6 ml of N,N-dimethylformamide, 93.1 g (0.783 mol) of thionyl chloride were added and were mixed at 60 to 65° C. for 20 hours. Subsequently, by depression, the solvent was recovered, followed by adding 415 ml of toluene, 271.9 g (2.089 mol) methacrylic acid 2-hydroxyethyl and were mixed at 80° C. for 15 hours. 400 ml of water was added thereto and the water layer of the bottom layer were separated at 70° C. and removed. The operation of adding 300 ml of water and separating and removing the water layer of the bottom layer at 70° C. was repeated for 3 times, followed by recovering the solvent by depression, to which 190 ml of isopropyl alcohol and 400 ml of water were added, further followed by cooling it to 5° C., and the generated sediment was filtered, rinsed, and dried thereby obtaining a coarse crystal. This coarse crystal was recrystalized to obtain 19.2 g of compound (a). The yield was 23% (from 5-carboxy-2-(2-hydroxy-4-methoxyphenyl)-2H-benzotriazole). A melting point was 116° C.

In the meantime, by HPLC analysis, a purity of the compound (a) was measured.

<Condition of Measurement>

Apparatus: LC-20AT (Shimadzu Corporation)

Column used: SUMIPAX ODS A-212 6.0×150 mm 5 μm

Column temperature: 25° C.

Mobile phase: methanol/water=95/5 (phosphoric acid 3 ml/L)

Flow velocity: 1.0 ml/min

Detection: UV250 nm

<Result of Measurement>

HPLC surface purity: 97.2%

For information, the HPLC measurement was conducted under the same measurement condition as above in the following Example 4 and Reference Examples 1 and 2.

Figure 1:
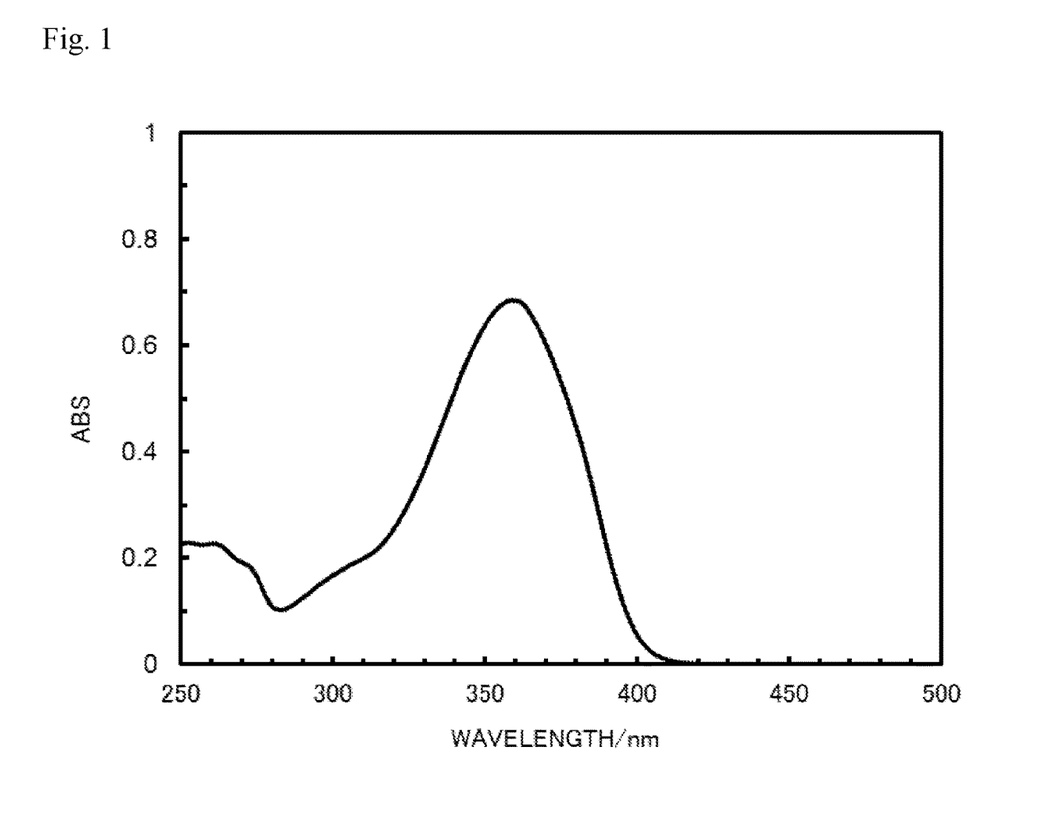
FIG. 1 shows UV~visible absorption spectrum of a compound (a).

The ultraviolet~visible absorption spectrum of the compound (a) was measured, and it was found that the maximum absorption wavelength λmax was 359.0 nm, and the molar extinction coefficient ε of the wavelength was 27800. The spectrum is shown in FIG. 1. The measurement condition of the spectrum is as follows:

<Condition of Measurement>

Apparatus: UV-2450 (Shimadzu Corporation)

Measurement wavelength: 250 to 500 nm

Solvent: chloroform

Concentration: 10 ppm

For information, the ultraviolet~visible absorption spectrum was measured under the same measurement condition as above in the following Reference Example 3 and Example 5.

Further, as the result of the NMR measurement of the compound (a), the above structure was supported. The measurement condition is as follows:

<Condition of Measurement>

Apparatus: JEOL JNM-AL300

Resonant frequency: 300 MHz (1H-NMR)

Solvent: chloroform

As an internal standard substance of 1H-NMR, tetramethylsilane was used, and the chemical shift value was represented by δ value (ppm) and the coupling constant was represented by Hertz. Further, s represents an abbreviation of singlet, d that of doublet, t that of triplet, and m that of multiplet. The same is applied to the following Examples 4 to 5 and Reference Examples 1 to 3. For information, in the following Examples 4 to 5 and Reference Examples 1 to 3, the NMR measurement was conducted as in the present Example. The content of the NMR spectrum obtained is as follows:

δ=11.27 (s, 1H, phenol-OH), 8.71 (m, 1H, benzotriazole-H), 8.32 (d, 1H, J=9.0 Hz, benzotriazole-H), 8.04 (m, 2H, benzotriazole-H, phenol-OH), 6.71 (d, 1H, J=3.0 Hz, phenol-H), 6.64 (m, 1H, phenol-H), 6.18 (m, 1H, C=$CH_2$—H), 5.62 (m, 1H, C=$CH_2$—H), 4.60 (m, 4H, methacryloyl-O—$CH_2$—$CH_2$—H), 3.94 (s, 3H, phenol-O—$CH_3$—H), 1.97 (m, 3H, $CH_2$=C—$CH_3$—H)

Example 4

Synthesis of compound [b]; 2-acryloyloxyethyl 2-(2-hydroxy-4-methoxyphenyl)-2H-benzotriazole-5-carboxylate

[Chemical 15]

Compound (b)

Compound (b) was obtained with the yield of 34% (from 5-carboxy-2-(2-hydroxy-4-methoxyphenyl)-2H-benzotriazole) in the same manner as in Example 3 except that acrylate acid 2-hydroxyethyl was used instead of methacrylate acid 2-hydroxyethyl. The melting point was 111° C. and the HPLC surface purity was 93.3%.

Figure 2:
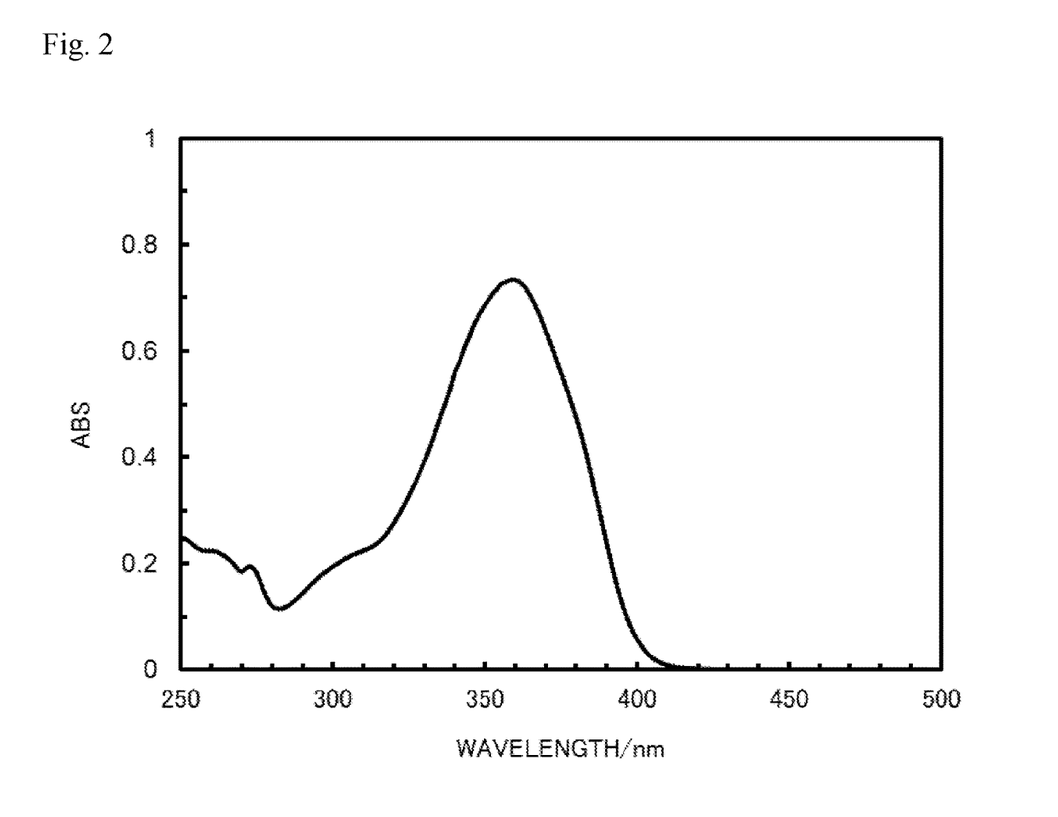
FIG. 2 shows UV~visible absorption spectrum of a compound (b).

Further, when the ultraviolet~visible absorption spectrum of the compound (b) was measured, the maximum absorption wavelength λmax was 358.6 nm, and the molar extinction coefficient ε of the wavelength was 27900. The spectrum is shown in FIG. 2. The measurement condition of the spectrum is as follows:

<Condition of Measurement>
  Apparatus: UV-1850 (Shimadzu Corporation)
  Measurement wavelength: 250 to 500 nm
  Solvent: chloroform
  Concentration: 10 ppm For information, the ultraviolet~visible absorption spectrum was measured in the following Reference Examples 1 to 2 under the same measurement condition as in the present Example.

Further, as the result of measuring the NMR of the compound (b), the above structure was supported. The content of the obtained NMR spectrum is as follows:

δ=11.23 (s, 1H, phenol-OH), 8.69 (m, 1H, benzotriazole-H), 8.28 (d, 1H, J=9.3 Hz, benzotriazole-H), 8.09 (m, 1H, benzotriazole-H), 7.92 (m, 1H, phenol-H), 6.69 (m, 1H, phenol-H), 6.61 (m, 1H, phenol-H), 6.45 (m, 1H, CH=CH$_2$—H), 6.20 (m, 1H, CH$_2$=CH—H), 5.87 (m, 1H, CH=CH$_2$—H), 4.58 (m, 4H, acryloyl-O—CH$_2$—H, acryloyl-O—CH$_2$—CH$_2$—H), 3.87 (s, 3H, phenol-O—CH$_3$—H)

Reference Example 1

Synthesis of compound (c); methyl 2-(2-hydroxy-4-methoxyphenyl)-2H-benzotriazole-5-carboxylate

[Chemical 16]

Compound (c)

Compound (c) was obtained with the yield of 46% (from 5-carboxy-2-(2-hydroxy-4-methoxyphenyl)-2H-benzotriazole) in the same manner as in Example 3 except that methyl alcohol was used instead of methacrylate acid 2-hydroxyethyl. The melting point was 185° C. and the HPLC surface purity was 96.0%.

Figure 3:
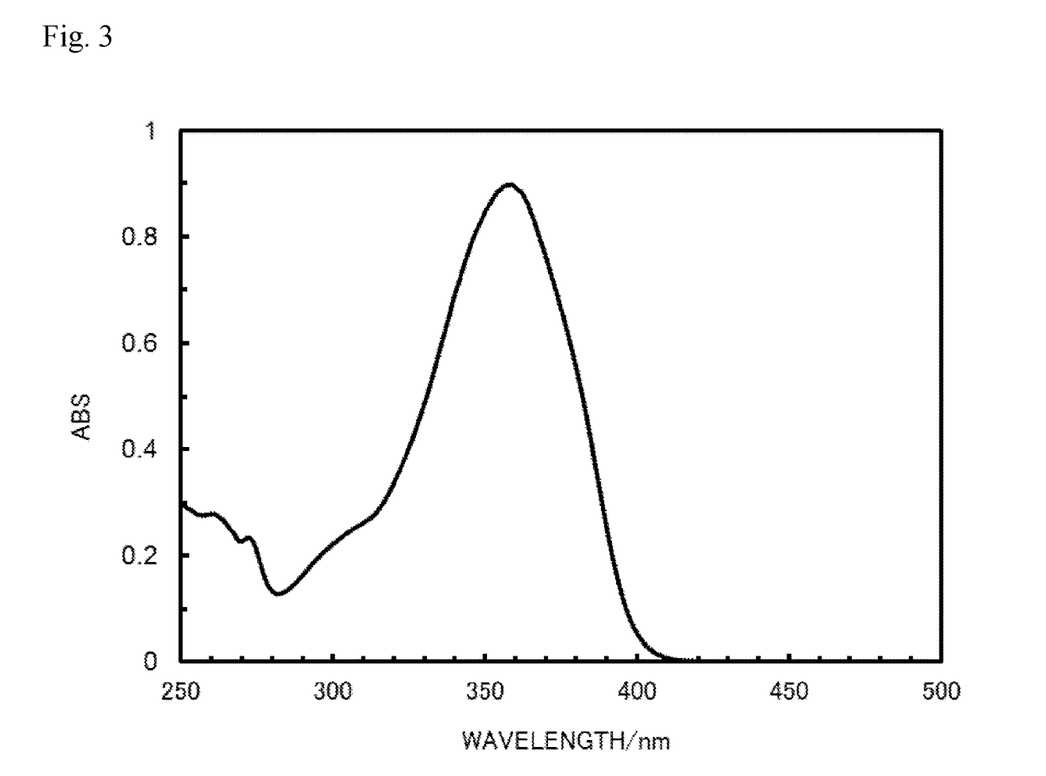
FIG. 3 shows UV~visible absorption spectrum of a compound (c).

The maximum absorption wavelength λmax was 357.8 nm, and the molar extinction coefficient ε of the wavelength was 26400. The spectrum is shown in FIG. 3.

Further, as the result of measuring the NMR of the compound (c), the above structure was supported. The content of the obtained NMR is as follows:

δ=11.23 (s, 1H, phenol-OH), 8.65 (m, 1H, benzotriazole-H), 8.26 (d, J=9.0 Hz, 1H, benzotriazole-H), 8.07 (m, 1H, benzotriazole-H), 7.89 (m, 1H, phenol-H), 6.67 (m, 1H, phenol-H), 6.59 (m, 1H, phenol-H), 3.86, 3.99 (each s, each 3H, phenol-O—CH$_3$—H and C=O—O—CH$_3$—H)

Reference Example 2

Synthesis of compound (d); 2-ethylhexyl 2-(2-hydroxy-4-methoxyphenyl)-2H-benzotriazole-5-carboxylate

[Chemical 17]

Compound (d)

Figure 4:
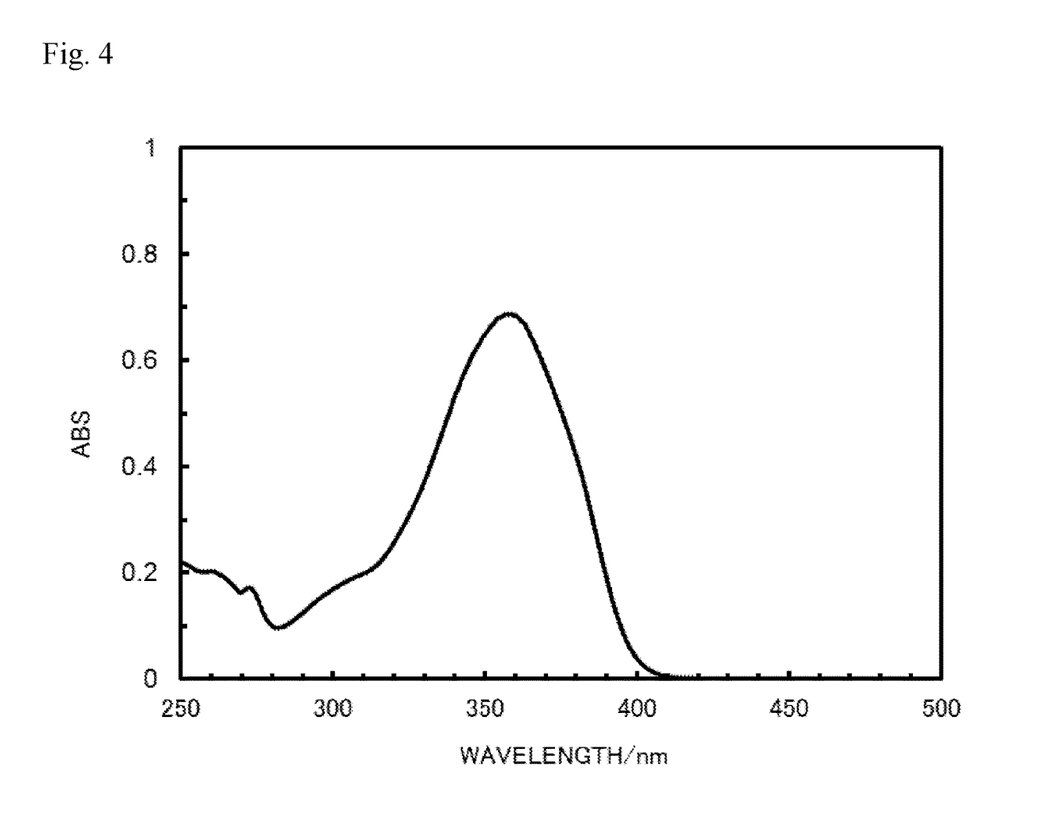
FIG. 4 shows UV~visible absorption spectrum of a compound (d).

Compound (d) was obtained with the yield of 28% (from 5-carboxy-2-(2-hydroxy-4-methoxyphenyl)-2H-benzotriazole) in the same manner as in Example 3 except that 2-ethylhexylalcohol was used instead of methacrylate acid 2-hydroxyethyl. The melting point was 56° C. and the HPLC surface purity was 98.2%. The maximum absorption wavelength λmax was 358.6 nm, and the molar extinction coefficient ε of the wavelength was 27800. The spectrum is shown in FIG. 4.

Further, as the result of measuring the NMR of the compound (d), the above structure was supported. The content of the obtained NMR is as follows.

δ=11.26 (s, 1H, phenol-OH), 8.67 (m, 1H, benzotriazole-H), 8.28 (d, 1H, J=9.3 Hz, benzotriazole-H), 8.09 (m, 1H, benzotriazole-H), 7.92 (m, 1H, phenol-H), 6.69 (m, 1H, phenol-H), 6.61 (m, 1H, phenol-H), 4.31 (m, 2H, benzotriazole-CO—O—CH$_2$), 3.87 (s, 3H, phenol-O—CH$_3$—H), 1.78 (m, 1H, 2-ethylhexyl-CH), 1.51 (m, 8H, 2-ethylhexyl-CH$_2$), 0.96 (m, 6H, 2-ethylhexyl-CH$_3$)

Reference Example 3

Synthesis of compound (e); octyl 2-(2-hydroxy-4-octyloxyphenyl)-2H-benzotriazole-5-carboxylate

[Chemical 18]

Compound (e)

To a four-neck flask of 1000 ml, a balled condenser, a thermometer, and a mixing device were attached, in which 106.0 g (1.340 mol) of pyridine was put to which 197.0 g (1.945 mol) of 36% hydrochloric acid was added taking time for 15 minutes and mixed for 1.5 hours followed by restoring 100 g of the solvent, thereby obtaining a slurry of pyridine hydrochloride. Subsequently, 20.0 g (0.067 mol) of 5-carboxy-2-(2,4-dimethoxyphenyl)-2H-benzotriazole was added, followed by mixing at 160° C. for 21 hours, further followed by cooling it to 70° C. to which 250 ml of water was added and the pH value was adjusted to 3 by an aqueous solution of 32% sodium hydroxide. Then, it was cooled to 30° C. and the generated sediment was filtered, rinsed, and then dried, thereby obtaining 18.1 g of 5-carboxy-2-(2,4-dihydroxyphenyl)-2H-benzotriazole. The yield was 100% (from 5-carboxy-2-(2,4-dimethoxyphenyl)-2H-benzotriazole).

Figure 5:
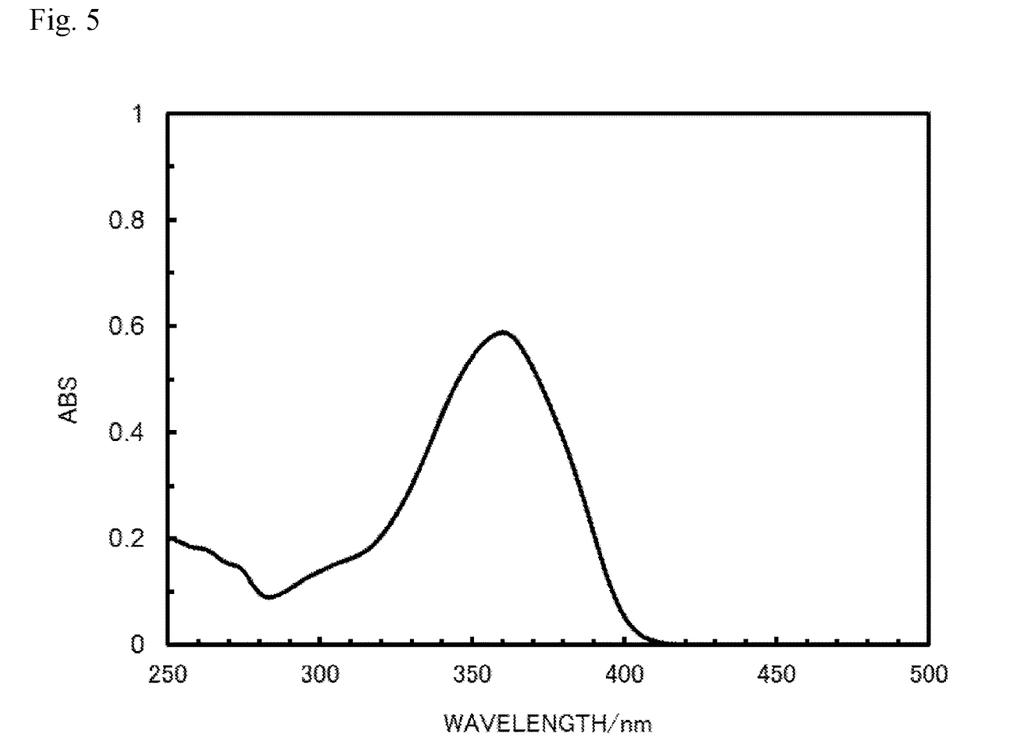
FIG. 5 shows UV~visible absorption spectrum of a compound (e).

To a four-neck flask of 300 ml, a balled condenser, a thermometer, and a mixing device were attached, in which 9.0 g (0.033 mol) of 5-carboxy-2-(2,4-dimethoxyphenyl)-2H-benzotriazole, 4.4 g (0.042 mol) of sodium carbonate, 11.8 g (0.079 mol) of octylchloride, 20 ml of N—N-dimethylformamide, 0.5 g of potassium iodide, and 1.3 g of polyethylene glycol 400 were put, and were mixed at 130 to 140° C. for 3 hours. Then, 100 ml of toluene and 100 ml of water were added and the water layer in the bottom layer was separated at 70 to 75° C. to be removed, to which 100 ml of water and 2 ml of acetic acid were further added, and the water layer in the bottom layer was separated at 70 to 75° C. to be removed. Toluene was recovered by depression and 40 ml of alcohol was added and then, the generated sediment was filtered, rinsed, and dried, thereby obtaining 5.6 g of a coarse crystal. This coarse crystal was recrystalized to obtain 4.7 g of compound (e). The yield was 29% (from 5-carboxy-2-(2,4-dihydroxyphenyl)-2H-benzotriazole). A melting point was 97° C. The maximum absorption wavelength λmax was 360.2 nm, and the molar extinction coefficient ε of the wavelength was 27600. The spectrum is shown in FIG. 5.

Further, by HPLC analysis, a purity of the compound (e) was measured.

<Condition of Measurement>
Apparatus: L-2130 (Hitachi High-Technologies Corporation)
Column used: SUMIPAX ODS A-212 6.0×150 mm 5 μm
Column temperature: 40° C.
Mobile phase: methanol/water=99/1
Flow velocity: 1.0 ml/min
Detection: UV250 nm
<Result of Measurement>
HPLC surface purity: 99.0%

For information, the HPLC measurement was conducted under the same measurement condition as in the present Reference Example in the following Example 5.

Further, as a result of measuring NMR of chemical compound (e), the above structure was supported. The content of the obtained NMR spectrum is as follows:

δ=11.26 (s, 1H, phenol-OH), 8.68 (s, 1H, benzotriazole-H), 8.29 (d, 1H, J=9.0 Hz, benzotriazole-H), 8.11 (d, 1H, J=8.9 Hz, benzotriazole-H), 7.93 (d, 1H, J=9.0 Hz, phenol-H), 6.69 (m, 2H, phenol-OH), 4.38 (t, 2H, benzotriazole-CO—O—CH$_2$—H), 4.01 (t, 2H, phenol-O—CH$_2$—H), 1.46 (m, 24H, octyl-CH$_2$), 0.91 (s, 6H, octyl-CH$_3$)

Example 5

Synthesis of compound (f); 2-methacloyloxyethyl 2-(2-hydroxy-4-octyloxyphenyl)-2H-benzotriazole-5-carboxylate

[Chemical 19]

To a four-neck flask of 200 ml, a balled condenser, a thermometer, and a mixing device were attached, in which 3.3 g (0.067 mol) of compound (e), 0.8 g (0.0200 mol) of sodium hydroxide, 25 ml of isopropyl alcohol, and 25 ml of water were put and mixed at 70 to 75° C. for 2 hours. 1 ml of 62.5% sulfuric acid were added to adjust the pH value to 5, followed by filtering, rinsing, and drying the generated sediment to obtain 2.5 g of 5-carboxy-2-(2-hydroxy-4-octyloxyphenyl)-2H-benzotriazole.

Figure 6:
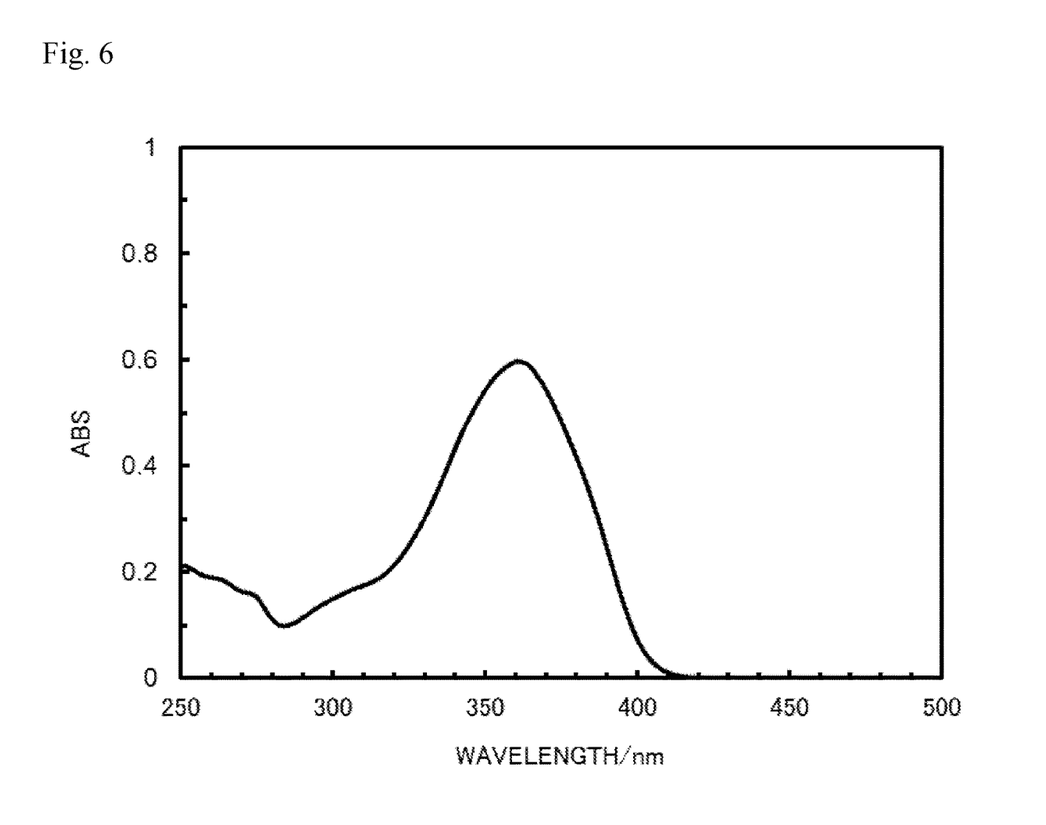
FIG. 6 shows UV~visible absorption spectrum of a compound (f).

To a four-neck flask of 2000 ml, a balled condenser, a balled condenser, a thermometer, and a mixing device were attached, to which 2.5 g (0.0065 mol) of 5-carboxy-2-(2-hydroxy-4-octyloxyphenyl)-2H-benzotriazole, 2.0 g (0.0168 mol) of thionyl chloride, 50 ml of toluene, and 0.2 ml of N,N-dimethylformamde were put and mixed at 62 to 68° C. for 1 hour. Toluene was recovered by depression and 50 ml of toluene, 1.8 g (0.0138 mol) of methacrylate acid 2-hydroxyethyl, and 1.3 g (0.0164 mol) of pyridine were added and mixed at 72 to 78° C. for 1 hour. Then, 30 ml of water and 0.5 ml of 62.5% sulfuric acid were added and the water layer in the bottom layer was separated at 70 to 75° C. to be removed, followed by recovering toluene by depression, further followed by adding 30 ml of isopropyl alcohol, further followed by filtering, rinsing, and drying the generated sediment thereby obtaining 2.2 g of a coarse crystal. This coarse crystal was recrystalized with isopropyl alcohol, to obtain 1.4 g of compound (f). The yield was 42% (from compound (e)). A melting point was 69° C. and the HPLC surface purity was 94.8%. The maximum absorption wavelength λmax was 360.8 nm, and the molar extinction coefficient F of the wavelength was 28700. The spectrum is shown in FIG. 6.

Further, as a result of measuring the NMR, the above structure was supported. The content of the NMR spectrum obtained is as follows:

$\delta$=11.24 (s, 1H, phenol-OH), 8.70 (m, 1H, benzotriazole-H), 8.31 (d, 1H, J=12.9 Hz, benzotriazole-H), 8.11 (d, 1H, J=10.5 Hz, benzotriazole-H), 7.95 (d, 1H, J=9.0 Hz, phenol-H), 6.69 (m, 2H, phenol-H), 6.18 (s, 1H, C=$CH_2$—H), 5.62 (s, 1H, C=$CH_2$—H), 4.64 (m, 2H, methacryloyl-O—$CH_2$—H), 4.56 (m, 2H, benzotriazole-CO—O—$CH_2$—H), 4.01 (t, 2H, phenol-O—$CH_2$—H), 1.97 (s, 3H, $CH_2$=C—$CH_3$—H), 1.45 (m, 12H, octyl-$CH_2$), 0.90 (s, 3H, octyl-$CH_3$)

Comparative Example

As a comparative example, a compound (g); 3-(2H-benzotriazole-2-yl)-4-hydroxyphenethyl methacrylate that is a conventionally general ultraviolet light absorber and a compound (h); 2-[2-(6-hydroxybenzo [1,3] dioxysol-5-yl)-2H-benzotriazole-5-yl]ethylmethacrylate that is a benzotriaole derivative compound having sesamol capable of powerfully absorbing the long wavelength range were synthesized.

(Preparation of an Ultraviolet Light Absorbing Film)

0.1 g of compound (a) obtained in Example 3, 1.9 g of polymethyl methacrylate, 4 g of methylethylketone, and 4 g of toluene were mized and dissolved to obtain a solution of a resin compound having an ultraviolet light absorber. Then the obtained ultraviolet light absorber was applied onto a glass plate (2 mm thick) by using a bar coater No. 20, followed by heating and drying at 90° C. for 2 minutes, then followed by heating and drying at 120° C. for 3 minutes. After that, drying under reduced pressure was implemented at 40° C. for 12 hours to remove the solvent thereby obtaining a film of polymethyl methacrylate having 5% ultraviolet absorber with the film thickness of 4 μm. In the meantime, the compounds (g) and (h) synthesized in Comparative Examples were respectively copolymerized with methyl methacrylate to prepare a copolymer that includes 5% ultraviolet absorber, followed by filming them by the same method as in compound (a) thereby obtaining a film of polymethyl methacrylate having 5% ultraviolet absorber with the film thickness of 4 μm.

[Ultraviolet Blocking Test]

By placing the film of polymethyl methacrylate having 5% ultraviolet absorber of the compounds (a), (g), and (h) that were obtained in the above mentioned methods on transfer films of yellow dyes, cyan dyes, and magenta dyes, that are used for commercially available sublimation transfer type compact photo printer (Canon SELPHY CP600) to protect the transfer films, followed by irradiating simulated solar light for 100 hours by a weather meter to see color fading. Five criteria were set in which Level 5 signifies no fading, level 4 little fading, level 3 fading to some extent, level 2 much fading and level 1 complete fading. The results evaluated based on the above are shown in Table 1.

TABLE 1

| | UV light absorbing film | | | |
|---|---|---|---|---|
| | Compound (a) | Compound (g) (Comparison) | Compound (h) (Comparison) | No film (Comparison) |
| Evaluation result of UV light blocking test | 5 | 3 | 5 | 2 |

[Measurement of Visible Light Transmittance]

Table 2 shows visible light transmittance in chloroform of the above compounds (a) and (h) that were obtained by the above method.

TABLE 2

| UV light absorber | | Compound (a) | Compound (h) (Comparison) |
|---|---|---|---|
| Transmittance/% | 440 nm | 96.3 | 34.3 |
| | 450 nm | 98.8 | 80.0 |
| | 460 nm | 99.4 | 92.5 |
| | 470 nm | 99.5 | 95.9 |

From Table 1, it is found that similar to a conventional compound (h) capable of absorbing long wavelength range, a compound (a) has a high ultraviolet light blocking function in a long term. Further, from Table 2, it is found that coloring is less in view of the higher transmittance in the visible light range of 440 to 470 nm compared with that of the compound (h). Therefore, it is found to be an effective ultraviolet absorber. For information, conditions of ultraviolet blocking test and the measurement of visible light transmittance of the compound obtained from the Reference Example and from the Comparative Example are as follows.

<Condition of Ultraviolet Light Blocking Test>

Apparatus: Superxenon weather meter SX-75 (Suga Test Instruments Co., Ltd)

Irradiation intensity: 180 W/$m^2$

Irradiation time: 100 hours

Black panel temperature: 63° C.

Tank moisture: 50%

<Condition of Measurement of Visible Light Transmittance>

Apparatus: UV-1850 (Shimadzu Corporation)

Measurement wavelength: 400 to 500 nm

Solvent: Chloroform

Concentration: 10000 ppm

INDUSTRIAL AVAILABILITY

The benzotriazole derivative compound of the present invention exhibits a maximum absorption wavelength in a vicinity of 360 nm, with excellent ultraviolet light blocking function while showing little coloration, and therefore, the ultraviolet light blocking function is not damaged even when exposed to solar light for a long time. Thus, it can be utilized for a material that deteriorates with ultraviolet light and for protection of a human body. In particular, it can preferably be used for the use where coloration is not desirable. Further, the benzotriazole derivative compound of the present invention can be synthesized with a high yield and therefore, it can be manufactured at a lower cost thereby capable of being used for wide uses.

The invention claimed is:

1. A benzotriazole derivative compound represented by the following general formula (1), General formula (1)

wherein in general formula (1), $R_3$ represents an alkyl group whose carbon number is 1 to 8, and $R_4$ represents an acryloyl oxyalkyl group whose alkyl carbon number is 1 to 2 or an methacryloyl oxyalkyl group whose alkyl carbon number is 1 to 2.

2. An ultraviolet light absorber containing the benzotriazole derivative compound according to claim 1.

3. An ultraviolet light absorbing resin compound wherein the benzotriazole derivative compound according to claim 1 is compounded in a resin.

* * * * *